(12) United States Patent
Bogaert et al.

(10) Patent No.: US 7,048,759 B2
(45) Date of Patent: May 23, 2006

(54) INTRAOCULAR LENSES

(75) Inventors: Theo T. M. Bogaert, Groningen (NL); Sieger T. Meijer, Zuidlaren (NL)

(73) Assignee: Advanced Medical Optics, Inc., Santa Ana, CA (US)

( * ) Notice: Subject to any disclaimer, the term of this patent is extended or adjusted under 35 U.S.C. 154(b) by 721 days.

(21) Appl. No.: 09/777,510

(22) Filed: Feb. 6, 2001

(65) Prior Publication Data

US 2001/0051826 A1    Dec. 13, 2001

Related U.S. Application Data

(60) Provisional application No. 60/188,470, filed on Mar. 10, 2000.

(30) Foreign Application Priority Data

Feb. 24, 2000    (SE)    .................................... 0000611

(51) Int. Cl.
  *A61F 2/16*    (2006.01)
(52) U.S. Cl. .................................... 623/6.17; 623/6.36
(58) Field of Classification Search ............... 623/6.17, 623/6.36, 6.24, 6.27, 6.3, 6.31, 6.25, 6.21, 623/6.32
  See application file for complete search history.

(56) References Cited

U.S. PATENT DOCUMENTS

| 4,414,694 A | 11/1983 | Choyce |
| 4,573,998 A | 3/1986 | Mazzocco |
| 4,585,456 A | 4/1986 | Blackmore |
| 4,676,792 A | 6/1987 | Praeger |
| 4,769,035 A | 9/1988 | Kelman |
| 5,071,432 A | 12/1991 | Baikoff |
| 5,201,763 A | 4/1993 | Brady et al. |
| 5,258,025 A | 11/1993 | Fedorov et al. |
| 5,300,117 A | 4/1994 | Baikoff et al. |
| 5,480,428 A | 1/1996 | Fedorov et al. |
| 5,652,014 A | 7/1997 | Galin et al. |
| 5,776,192 A | 7/1998 | McDonald |
| 5,913,898 A | 6/1999 | Feingold |
| 5,928,282 A | 7/1999 | Nigam |
| 6,092,899 A * | 7/2000 | Wanders ..................... 351/161 |
| 6,106,553 A * | 8/2000 | Feingold ..................... 623/6.36 |

FOREIGN PATENT DOCUMENTS

| CA | 2093097 | 10/1993 |
| GB | 2217210 | 10/1989 |
| WO | WO 8902252 | 3/1989 |
| WO | WO 9305732 | 4/1993 |
| WO | WO 9507059 | 3/1995 |
| WO | WO 9515733 | 6/1995 |

(Continued)

*Primary Examiner*—Danton DeMille
(74) *Attorney, Agent, or Firm*—Dinsmore & Shohl LLP

(57) ABSTRACT

The present invention relates to an intraocular correction lens for implantation in the posterior chamber of the eye between the iris and the intact natural lens. The lens has a concave posterior surface which is part of a non-spherical surface that is rotation symmetric around the optical axis of said optical part, wherein the intersection between said non-spherical surface and any plane containing the optical axis of the lens represents a flawless curve free from discontinuities and points of inflection. The invention also relates to methods of selecting correction lenses based on estimations of the individual eye in need of vision correction and thereby arriving with a correction lens with a high safety for wearer with respect to surrounding eye tissues.

54 Claims, 4 Drawing Sheets

FOREIGN PATENT DOCUMENTS

| WO | WO 9817205 | 4/1998 |
| WO | WO 9856315 | 12/1998 |

* cited by examiner

INTRAOCULAR LENSES

This application claims the benefit to Provisional Application No. 60/188,470 filed Mar. 10, 2000.

DESCRIPTION OF INVENTION

The present invention refers to implantable phakic intraocular lenses (IOLs) suitable as correction lenses together with the intact natural crystalline lens. The inventive lenses are provided with a posterior surface, which admits a more anatomical fit in the posterior chamber of the eye, thereby minimizing the risks of disturbing the natural lens.

BACKGROUND OF THE INVENTION

As a consequence of that surgical procedures in the eye when replacing a defect natural lens have been more perfected and less traumatic, for example after the development of resilient lenses capable of being folded through a small incision in the eye, phakic intraocular lenses are increasingly conceivable as an alternative to correct for optical deficiencies besides spectacles and conventional contact lenses.

In a general sense phakic lenses can be considered for implantation, either in the anterior (front) chamber of the eye between the cornea and the iris, or in the posterior (rear) chamber located between the iris and the natural crystalline lens.

Phakic lenses positioned in the anterior chamber have been considered as desirable in several earlier embodiments for the reason that this chamber is considerably larger than the posterior chamber and thereby admitting a less complicated surgical process. However, these types of lenses show series of drawbacks essentially related with an irritation action from the support means (haptics) on the sensitive eye structures. For example, the support means can, when positioned in the corner between cornea and iris, disturb the aqueous outflow and consequently generate an increase in the intraocular pressure, a condition, which at worst may induce glaucoma. Pressure on the support means on the anterior chamber angle can disturb blood circulation and cause pupil ovalization. Further, the support means and the optic may come in contact with the corneal endothelium and cause endothelial dystrophy with resulting loss of corneal transparency. Alternatively, the support means have been suggested to be fixated directly to the iris by various attachment means. A negative consequence of iris fixation is irritation of the iris.

It is a general complication when designing IOLs to be implanted in the posterior chamber between the iris and the natural crystalline lens that the available space is small. Consequently, the lenses cannot be bulky as frequently is required when a high power optical correction is considered. In particular, consideration must be taken to avoid or restrict any contacts with the intact natural crystalline lens, in order to prevent it from damages, which may lead to local opacifications, or at worst case cataract formation.

Considerations must also be taken to that contact with iris could result in abrasive damages with resulting pigment dispersion and that the pupil must not be blocked, so the flow of aqueous humor is prevented which may lead to raised intraocular pressure and reduced circulation of nutrients and metabolites to and from the natural crystalline lens.

U.S. Pat. No. 4,585,456 (Blackmore) discloses an early version of a posterior chamber phakic IOL that is fixed in position by appendages that contact the ciliary sulcus. In the embodiments described herein no considerations have been taken to minimize contact with surrounding sensitive eye structures.

U.S. Pat. No. 4,769,035 (Kelman) also describes a method of correcting eyesight with an IOL positioned between the iris and the natural lens. The method involves a step of determining the shape of the natural lens in its flattest natural condition (i.e. non-accommodated) and forming a posterior surface of the IOL which has a curvature conforming with the natural lens in said condition. The resulting IOLs will be in permanent contact with the natural lens, which means that there will be a risk that damages are caused in its structure with cataract formation as a consequence.

To minimize the risk of contacting the natural lens several designs have been suggested where the lens is provided with supporting means to secure to the ciliary sulcus. U.S. Pat. No. 5,258,025 (Fedorov) relates to a correction IOL for implantation between the iris and the natural lens having modified supporting elements with a tapered peripheral part serving to protect the ocular tissues from such interaction with the lens that could result in postoperative inflammations.

European Patent 0 563 602 (Chiron Adatomed) discloses a correction lens for the posterior chamber of the eye provided with an outer haptic portion designed so as to distance the correction lens from the natural lens while enabling a securing contact with the zonule fibers of the ciliary sulcus in order to properly define the lens position. The geometric configuration of the correction lens and the presence of openings for fluid circulation in the haptics serve to provide for that the anterior surface of the natural lens remains accessible for the metabolic processes occurring at this location.

Fixating correction lenses in the ciliary sulcus is not preferred, because the sulcus has an irregular shape varying between different individuals and it will be difficult to accurately size the overall lens length. It will either be to short, or have an unpredictable central distance to the natural lens, which means that the optical correction cannot be sufficiently controlled. It is another disadvantage that the correction lens is in a fixed in a predetermined position when the pupil is off-center. Further, the force of the sulcus-fixated lens exerted on the ciliary tissues increases the risk of a blood/aqueous barrier break.

It has therefore been suggested to design correction lenses for the posterior chamber to float on a layer of aqueous humor in front of the natural lens, without having any permanent securing contact with the ciliary sulcus periphery and follow the movements of the pupil. The length of a free floating lens is smaller than the sulcus diameter and the lens will rest on the zonula or be pushed forwards by the aqueous humor secreted by the ciliary body. The aqueous flow can thereby more easily reach the entire surface of the lens and bring nutrients to the natural lens surface and remove derivatives from its metabolic process.

International Patent Applications published as WO 89/02252 (Mezhotraslevol Nauchno-Tekhnichesky Komplex "Microkhirurgia Glaza") and WO 95/15733 (Voir Et Vivre) disclose floating corrective IOLs for the posterior chamber wherein the supporting elements (haptic part) of the lens are considerably smaller in diameter than the ciliary sulcus and the lenses are secured in a corrected position by iris contact from dilations of the pupil acting on the optical part which protrudes into the anterior chamber of the eye. These lenses suffer from the drawback from that their optical parts have a limited diameter and that the edge of the optical part can scatter light with the result of undesired formation of halo-shaped optical sensations.

U.S. Pat. No. 5,480,428 (Fedorov) discloses a floating posterior chamber correction lens with a protruding optical part centered by the iris. In order to enable fluid circulation, in case the pupil is blocked by the lens, the optical part is provided with a central hole thereby avoiding the need of creating a hole in the iris (iridotomy). Further, this lens has a positioning element with a posterior surface having a radius largely following that of the natural lens, which is larger than the radius of the posterior surface of the optical part. This design means that the lens will be bulky, especially if a high refractive outcome is desired, so that the lens may be pushed forwards and apply a force against the iris by the pressure exerted from accommodation of the natural lens. Permanent disturbances of the iris can at worst induce pigment dispersion followed by pigmentary glaucoma. There is also a risk that a permanent forward dislocation of the iris can lead to that the anterior chamber angle closes the trabecular meshwork involved in aqueous humor transportation. When this condition is permanent the intraocular pressure can be chronically raised.

U.S. Pat. No. 5,913,898 (Feingold) discloses a corrective lens for the posterior chamber of the eye provided with features on its anterior side that enables a more smooth contact with the iris so as to avoid damages of wear due to long term contact. This patent also discloses means for allowing sufficient circulation of eye fluids around the lens, so as to avoid the built up of pressure differences between the posterior and the anterior chambers of the eye.

WO 98/17205 (IVI) discloses a farther developed floating corrective lens for the posterior chamber wherein more considerations have been taken to the interaction with iris by making the lens thinner and having the optic part substantially in the posterior chamber. However, this lens design cannot avoid pupillary block of circulating fluids, so the need of applying iridotomies (holes in the iris) remains. Further, these lenses do not consider any precautionary means to avoid damages to the zonulas and to surface of the natural lens.

Even if efforts are made in the corrective lenses for the posterior chamber to avoid disturbing the highly sensitive natural lens and thereby risk to induce the formation of opaque areas or a cataract, there still is a need to develop a lens having a posterior surface that contributes to avoid or decrease the risk of inflicting damages to the natural lens or to the zonulas. As will become apparent in the below in the descriptive part and the objects of invention, the presently inventive lens aims to provide a solution to these problems.

It is an object of the present invention to provide a corrective lens having an improved adaptation to the free space available in the posterior chamber of the eye between the iris and the natural lens so as to avoid any disturbances to the natural tissues.

It is another object of the present invention to provide a corrective lens for the posterior chamber of the eye that minimizes the contacts with the natural lens so as to avoid the cataract formation.

It is a further object of the present invention to provide a corrective lens having a posterior surface facing the natural lens designed to avoid stress concentration in this region.

It is a still further object of the present invention to provide a corrective lens with supporting means, which are adapted so as to avoid inflicting damages to the zonulas or to the ciliary sulcus.

These and other objects of the invention, which will be described in more detail below, or will be obvious from later explanations, are met with the presently invented lenses as disclosed in the following descriptive sections.

DESCRIPTION OF THE INVENTION

In the most general terms, the present invention pertains to an intraocular correction lens for implantation in the posterior chamber of the eye between the iris and the intact natural lens. The correction lens comprises a centrally located optical part capable of providing an optical correction and a peripherally located supporting element capable of maintaining said optical part in the central location. If regarded from above, the correction lens will generally have total length from about 9 to about 13 mm and a width from about 6 to about 8 mm which values are confined by the size of the posterior chamber of the individual patient. In accordance with the present invention, the optical part and the support element together have a concave posterior surface, which after implantation will face the natural lens. The concave posterior surface is a part of a non-spherical surface that is rotation symmetric around the optical axis of said optical part. The intersection between the non-spherical surface and any plane containing the optical axis represents a flawless curve free from discontinuities and points of inflection. A representative flawless curve is formed by the intersection of a plane containing both the optical axis and the longest symmetry axis of the lens contour and said non-spherical surface.

In the context of the present invention, a flawless curve free from discontinuities is defined by that the curve is expressed by a continuous mathematical function. Further, that the curve is defined to be free from points of inflection is defined herein as the mathematical function defining, or approximating, the curve should not have any points of inflection, i.e. the second derivative of the mathematical function is not equal to zero at any point of the curve. In order to conceive the curves, a contemplated cylindrical coordinate system is introduced having a z-axis coinciding with the optical axis and radius r/angle $\theta$ coordinates in a plane perpendicular to the optical axis and the origin of vertex of the correction lens. In the outlined coordinate system the above-mentioned flawless curve will be represented by a mathematical function $z=f(r,\theta)$, wherein r has positive value, having an extreme point on the z-axis (optical axis) and no points of inflection. The coordinate system is demonstrated in FIGS. 1 and 2 in the detailed part of the description.

According to one aspect of the invention, the posterior flawless curve of the correction lens is at least extended in a direction towards the lens periphery within an area defined by the projection of the natural lens on the posterior surface of said correction lens in a direction parallel to the optical axis. According to another aspect of the invnetion the posterior flawless curve of the lens has substantially the same extension as the width of the lens, i.e. a total length of from about 6 to 8 mm symmetrically distributed around the optical axis.

The natural lens typically varies in diameter between about 9 and 10.5 mm, depending on the individual patient and his/her age. The diameter of the natural lens can be estimated as a part of the pre-surgical considerations and a suitable correction lens with a suitably extended flawless curve can thereby readily be selected. The flawless curve should at least be extended in a direction towards the lens periphery within an area defined by the projection of the zonula-free natural lens on the posterior surface of said correction lens in a direction parallel to the optical axis.

Zonula free is defined herein, as the part of the lens that is substantially free from zonulas attached to the lens, through which the state of accommodation of the lens is regulated by the ciliary muscles. The extension of the flawless curve sufficiently covers the natural lens, thereby providing for that no local pressure points are built up that can form stress concentration points or zones on the natural lens which may impair its natural metabolism and form local opacifications which in worst case result in cataract formation and the subsequent need of surgical intervention.

The support elements comprise an inner part neighboring the optical part and an outer, peripheral part, which is designed to at least partially to be in contact with the ciliary sulcus and the zonulas. According to a first embodiment, the peripheral part is flawlessly connected to the inner part of the support elements. The flawless curve as defined above will thereby continue and extend in a peripheral curve which is defined as the intersection between a plane containing the optical axis and the peripheral part of the posterior non-spherical surface. According to another embodiment, the peripheral part of the support elements is connected to the inner part at a point of inflection of the curve represented by the intersection of the non-spherical posterior surface of correction lens and a plane containing the optical axis.

In accordance with a preferred embodiment, the peripheral part of the support means follows a curve that converges towards a plane perpendicular to the optical axis. This ensures that the support means are directed from the zonulas attached to the natural lens and that the lens advantageously adapts to be accommodated in the free space confined by the posterior chamber of the eye between the iris and the natural lens.

When the posterior surface is designed according to the invention, it is highly preferred that the central radius of the posterior concave surface of the optical part is different than the central radius of natural lens in its non-accommodated state. In this context, the central radius (of the posterior surface) is defined as the radius in the near proximity of the intersection of the optical axis and the correction lens and the natural lens, respectively. Accordingly, by selecting different radii, the risk of adherence between the implanted lens and the natural lens is avoided. In a first embodiment, the central radius of the posterior surface is substantially smaller than the central radius of the natural lens. Preferably, the central radius of the posterior surface is less than about 8 mm and more preferably less than about 7 mm. This embodiment is suitable for young patients less than about 30 years. In a second embodiment, especially suitable for patients older than about 30 years, the central radius of the posterior surface of the correction lens is substantially larger than the central radius of the natural lens. Preferably, the central radius of the posterior surface of the correction lens is larger than about 12 mm and more preferably larger than about 14 mm.

According to a specific embodiment, the radius of the posterior surface increases from the central part proximal to the optical axis towards the periphery. In this embodiment, at a point proximal to the periphery of the optical part the radius will be larger than at a central point proximal to the optical axis.

When designing the lenses of the present invnetion, the central radius of its posterior surface is determined with respect to an estimated value of the radius of the anterior surface of the natural lens in its non-accommodated state, measured by optical techniques. The anterior chamber depth, being the distance between the vertex of the cornea and the apex of the natural lens in rest and during accommodation, can be measured by means of ultrasonic equipment. Combining the values of the selected central radius and the estimated change in anterior chamber depth will result in the determination of the required minimal lens vault (see the definition in FIG. 2 for a definition of vault). The vault needs to be sufficiently large to avoid substantial intermittent contacts between the correction lens and the natural lens, but on the other hand the vault needs to be limited in order to avoid deformation or hindering of the iris. In order to fine tune the value of posterior radius, the radius of the anterior surface of the natural lens can be estimated in accommodated state so as to even more safely avoid significant intermittent contact outside the central part of the optic during accommodation. By estimating acceptable vault and posterior radius ranges, a specific lens with an acceptable vault and posterior central radius of a desired optical power can be selected.

In order to model the flawless curve as defined above different principles can be approached which are previously employed in optics for designing aspherical lenses, i.e. designing the anterior surface of a lens to reduce the spherical aberration (errors in refraction due to the spherical shape of a lens), for example in accordance with OSLO version 5 Program Reference, Chapter 4 (Update), Sinclair Optics 1996.

In a first aspect, the flawless curve comprises two or more tangentially attached circle segments. According to one embodiment of this aspect the flawless curve comprises three tangentially attached circle segments. For example, the three tangentially attached circle segments consist of a centrally located segment having a radius different to that of the natural lens in its non-accommodated state and two peripheral segments. In this specific example, the centrally located segment corresponds to the optical part and the peripheral segments correspond to the inner part of the support element. The three tangentially attached circle segments may thereby together form a fragment of an ellipsoidal curve.

In an other aspect, the flawless curve substantially follows the curve formula $z=cvr^2/(1+\sqrt{(1-cv^2(cc+1)r^2)})$, where z is the axial coordinate of the curve, r is the radial coordinate of the curve, cv is the reciprocal central radius (1/rd where rd is the radius of curvature) of the optical part and cc is the conic constant to shape the curve which not is equal to zero. These curves are generally called conic curves. The conic constant can generally be selected according the following chart:

| | |
|---|---|
| $CC = 0$ | Sphere |
| $CC = -1$ | Paraboloid |
| $CC < -1$ | Hyperboloid |
| $-1 < CC < 0$ | Ellipsoid |
| $CC > 0$ | Oblate Spheroid |

These curve designs are well known to optically skilled persons to model lenses having optics from corrected from spherical aberration. For example, conventional ocular lenses can be designed to deviate from a sphere in the peripheral region of their front (anterior) surfaces. However, in contrast to the present invention, the aspherical curve designs have been employed to model posterior surfaces of correction lenses. The design can be further optimized by adding one or several additional polynomal factors $a_1r^4+$ $a_2r^6+a_3r^8+a_4r^{10}+\ldots+a_nr^{2(n-1)}$), wherein $a_1, a_2, a_3, a_4, \ldots a_n$ are aspheric constants, thereby generating the curve formula:

$$z=cvr^2/(1+\sqrt{(1-cv^2(cc+1)r^2)})+a_1r^4+a_2r^6+a_3r^8+a_4r^{10}+\ldots+a_nr^{2(n-1)}$$

The selection of a posterior surface and a flawless curve design for a correction lens for the posterior chamber will in accordance with this aspect depend on the design of the optical part and the optical correction which has been determined as desirable for the patient. For example, if the optic is highly negative powered, i.e. more negative than about −15 diopters, the lens will have a convex-concave shape with a considerably thick edge profile (edge thickness) of the optical part which after implantation will consume a substantial volume of the available space in the posterior chamber of the eye. In such a case, the radius of the posterior surface proximal to the optical axis should be substantially smaller than radius of natural lens, i.e. less than about 8 mm, in order to avoid central adherence and to prevent deformation of the iris. A posterior surface can thereby be calculated and provided with a curve formula according to above, which will be substantially parabolic or hyperbolic. In another example, the lens is determined to have a positive power and the optic part will have a concave-concave shape with a central part proximal to the optical axis that will protrude anteriorly in the direction of the anterior chamber. The edge thickness of the optical part will be small and a posterior surface with a central radius larger than that of the natural lens is selected, i.e. larger than about 12 mm. The flawless curve representing the posterior surface will then be designed to bend towards the zonulas in the periphery and substantially follow an ellipsoidal curve formula.

In accordance with further aspects of the present invention, the flawless curve representing the posterior surface can also be constructed by other formulas and methods, e.g. by means of so-called Non uniform rational B-splines (NURBS), as referred to in I Piegl and W Tiller, The NURBS Book $2^{nd}$ Ed, N.Y., Springer-Verlag 1997.

It is an important aspect of the present invention that the corrective lenses for the posterior chamber shall be freely floating in the aqueous humor of the posterior chamber and not having a permanent engagement with ciliary sulcus constituting its inner periphery. A free floating lens is consequently not kept in a constant position by the ciliary sulcus, but will to certain degree follow the eye movements, i.e. those of the natural lens during accommodation and the dilations of the pupil, while being surrounded by the aqueous humor flowing through the zonulas in anterior direction. For this reason, lenses according to the present invention, preferably will have a maximum diameter (including optic part and support means, i.e. haptic part) less than the average diameter of the ciliary sulcus. Suitably, the overall length of the lens (maximum diameter) is should not be less than about 1 mm than the ciliary sulcus to avoid excessive decentration of the lens from the optical axis. The overall lens length according to the invention is generally a compromise to obtain a floating effect and while retaining a centering effect from the sulcus. Therefor, the presently invented lenses will be centered by a combined controlled interaction with the iris and the ciliary sulcus. It is to be understood that the sulcus in practice is not circular, but rather elliptical and irregular, so a frequent touching contact of between the lens and the sulcus will in reality be attained which contributes to the mentioned centering effect. Should the correction lens not be sufficiently centered by the iris movements or the forces of the aqueous fluid between the correction lens and the natural lens, excessive decentration will prevented by the sulcus. For this reason and since the sulcus diameter has a tendency to shrink with increasing age of the patient, it cannot always be avoided that the overall length (maximum diameter) of the lens at least at some points exceeds the sulcus diameter. For lenses having a large diameter (above about 10.5 mm) the probability of sulcus contact increases considerably and thereby the risk of sulcus engagement that may lead to a compression of the lens and its axial displacement. However, by forming a peripheral part of the support means (haptic part) in accordance with the present invention this problem can be overcome for lenses having a larger diameter.

As earlier described, the support element comprise an inner part neighboring the optical part and a peripheral part which will at least partially to be in contact with the ciliary sulcus and the zonulas. The posterior surface of the support means have been earlier described so as to follow the flawless curve in a peripheral direction extending at least along the inner part.

At the anterior side, the inner part of the support element will comprise a tapered transition zone, surrounding the generally circular optical zone. The transition zone will extend from the edge of the optical part and smoothly decrease in crossectional thickness until a constant thickness of the inner part is reached.

According to a specific embodiment of the present invention, the peripheral part of the support means consists of two separate diametrically opposite, symmetrical parts. Preferably, each of the peripheral parts of the support means are provided with at least one peripherally located indentation of a generally concave shape extending inwards towards the inner part of the support means and the optical axis. Preferably, the indentation extends at its deepest point to the inner part of the support means and thereby generally divides each peripheral part into two identical sections which will at least partially be in contact with the ciliary sulcus, as earlier explained. From the mentioned indentations at least two diametrically opposite free spaces will after implantation be formed in the region between the peripheral parts and the ciliary sulcus wall. The preferred depth of the indentations is between about 0.5 to 1.25 mm. The indentations thereby form free spaces, which will both contribute to fluid circulation around the lens and to that the contact between the lens and the sulcus is restricted by these resilient peripheral members in a manner that the floating effect of the lens can be maintained, while the benefit of the contributory lens centering effect from the sulcus contact is retained.

The optical part of the correction lens is as mentioned above essentially circular and can be designed to correct various optical defects, including myopia and hyperopia. For example, the inventive correction lenses can be designed to correct astigmatism by designing their anterior surface toroidal or superimposing a cylindrical surface on the anterior side of the lens. As another example, the inventive lenses can correct presbyopia by applying a bi- or multifocal surface of the anterior side of the lens. The optically skilled person can readily apply a number of alternative anterior surfaces to provide a desired optical correction.

The size of optical part (the optical diameter) generally varies between about 4 to about 7 mm dependent on the patient and the desired optical correction. The presently invented correction lenses, having the aforedescribed posterior surfaces represented by a flawless curve, are more adapted to the available space for implantation of the posterior chamber. This provides that integrity of the surrounding eye tissues can be maintained and results in that a greater freedom of designing the optical part is admitted. It is of a particular advantage that larger optical parts having a diameter of at least about 5.5 mm can be selected also for optics with high refractive power which otherwise risk to bulky and negatively interfere with the natural lens. This will give the benefit of providing corrective lenses having an optical part substantially larger than the dilated pupil which results in less edge glare and undesired halo or cusp effects for the lens wearer when imaging strong light in darkness. It is therefore an important aspect of the invention to be able to provide lenses with reduced edge glare for high negative power lens having a refractive power less than about −15 diopters or high positive power lenses having a refractive power higher than about +15 diopters. Preferably, such high power lenses have an optical part larger than about 5.5 mm.

The present invention further relates to a method of selecting an intraocular correction lens adapted for the implantation in the posterior chamber of the eye. The method enables that a lens can be individually tailored for a patient and be manufactured prior to surgical intervention based on routine measurements of the eye. The selective method comprises the steps determining the power of optical correction needed for restoring the vision of the patient and estimating the anterior radius of the natural lens in its non-accommodated state. From this determination, a posterior central radius of the correction lens different to that of the natural lens in its non-accommodated state is selected and the total lens vault, as defined in the appended FIG. 2, is determined. A flawless curve free from points of inflection can thereby be designed or selected from a number of suitable design alternatives. As earlier defined, the flawless curve represents the intersection of the posterior surface and a plane containing the optical axis, so as to provide an aspheric posterior lens surface. The flawless curve will typically follow the alternatives outlined earlier and will provide a posterior surface that extends sufficiently beyond the extension of the natural lens so as to avoid the discussed drawbacks resulting from a built-up local pressure. In addition, the method can involve estimation of the anterior radius of the natural lens in its accommodated state and the estimation of the anterior chamber depth, preferably both in the accommodated and the non-accommodated states. From one or several of these values and the mentioned values of the anterior radius in its non-accommodated state and the posterior central radius selection, a total lens vault can be determined having a sufficient safety margin to avoid contacts between the natural lens and the posterior surface of the correction lens. Further measurements of the eye involves estimation of the diameter of the ciliary sulcus and an adaptation of the total lens diameter to this value. As earlier mentioned, the ciliary sulcus has an irregular shape varying between different individuals. For these purposes an average diameter value of the ciliary sulcus can serve as a basis for selecting suitable overall lens diameter and thereby considering that the correction lens preferably only should be in partial contact with the sulcus.

Based on the estimation of the necessary optical correction and above-mentioned eye measurements of the individual patients sufficient data can be transferred to the lens manufacturer so an individually adapted lens can be supplied. Alternatively, the surgeon can select the most suitable lens from a kit of pre-manufactured lenses with posterior aspherical surfaces according to the present invention by employing an algorithm. In such a selective method, it also conceivable to fine-tune the maximum diametric length of the correction to the individual ciliary sulcus estimation of the patient. This can be performed by a final corrective cutting of the lens before implantation by means of conventional mechanical tools or by means of an ophthalmic laser.

The kit contains lenses having a range of different optical powers with dimensional features resulting from an estimation of a suitable average population. In this case, it is to be understood that the surgeon is provided with an algorithm capable of transferring the physiological data to a suggested lens and from this result select the most appropriate lens present in the kit.

The lenses according to the present invention can be made from conventional biocompatible optically clear materials of a suitable refractive index by suitable molding technologies. Depending on the material, the lenses can be molded in one singular piece (silicones or poly(methyl)methacrylate (PMMA)) or be machined by precision milling and lathe cutting (PMMA or hydrogels). The lenses can be made from stiff materials like PMMA and similar acrylates. Alternatively, the lenses can be made of a material that is foldable or compressible like polysiloxanes, hydrogels such as poly-HEMA, soft acrylates and the similar. A particularly suitable polysiloxane material is described in U.S. Pat. No. 5,306,297 and a particularly suitable hydrogel is described in U.S. Pat. No. 5,717,049. The skilled person can readily conceive alternatives to these materials for the inventive correction lenses.

The corrective lenses will be described in more detail below according to a specific embodiment that serves to illustrate a non-limiting example of the present invention.

DETAILED DESCRIPTION OF THE INVENTION

FIG. 1 and FIG. 2 show the contemplated cylindrical coordinate system and its application in a lens implanted in the eye, wherein the z-axis coincides with the optical axis of lens.

The following example aims to demonstrate the design considerations when outlining a posterior surface according to the present invention. References are given to FIG. 2 to 6.

EXAMPLE 1

Figure 3A:
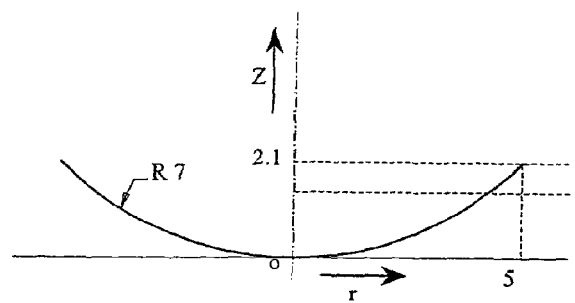
FIG. 3A, 3B and 3C show posterior curve designs from circles or circle segments with discontinuities and inflection points.
Figure 3B:
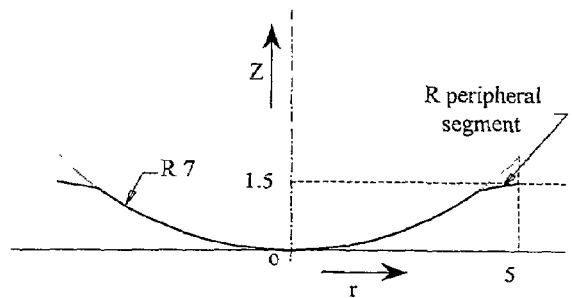
Figure 3C:
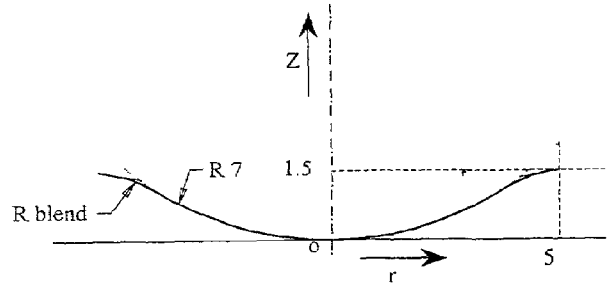
Figure 4:
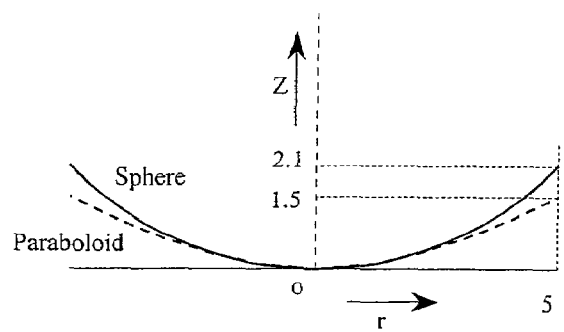
FIG. 4 shows a paraboloid curve design

After estimation of the front radius of the natural lens of a patient, a 7 mm central posterior radius of the correction lens implant is selected. This selection enables that any adherence to the natural lens is avoided. In order to avoid any contacts with the natural lens, the correction lens should rest on the zonulas and vault over the natural lens. The vault is defined in accordance with FIG. 2. A vault of 1.5 mm is assumed to be sufficient to avoid contact, both with the accommodated and the non-accommodated natural lens. Should the posterior surfaces be spherical with a radius of 7 mm over 9 mm, the central vault of the correction lens is 2.1 mm as shown in FIG. 3A which is too large when considering the dimensions of the posterior chamber. In order to reduce the vault, the posterior surface is constructed from circle segments. The central circle segment thereby represents the posterior surface of the optical part and the peripheral segment represents the posterior surface of the inner part of the support means. As shown in FIG. 3B, the junction of the central segment to the peripheral segments shows a discontinuity. When the correction lens is pressed towards the crystalline lens by the iris, the posterior surface at this junction will be responsible for a circle shaped stress concentration at the surface of the natural crystalline lens with the effect that the central area between the natural lens and the correction lens will be sealed off from communication with fresh aqueous humor. The stress concentration can also result in damage of the anterior capsule of the natural lens. The transition zone between the two circles can be blended to obtain a smooth transition as demonstrated in FIG. 3C. This will reduce the potential stress concentration, but not entirely eliminate the risks of its appearance. The blended transition zone of FIG. 3C will decrease the optical zone or can change the refractive properties of the lens in an uncontrolled manner. In order to overcome these drawbacks a flawless posterior parabolic surface is designed as shown in FIG. 4. The central radius of surface is 7 mm and the surface is constructed as a conic surface following the curve:

$$z = cvr^2/(1+\sqrt{(1-cv^2(cc+1)r^2)})$$

having a conic constant and an inverted central radius of curvature $cv=0.143$ mm$^{-1}$, resulting in a vault of 1.5 mm. The central part of the corrective implant still has optical properties if the anterior surface is spherical. This surface will vault sufficiently over the natural lens and it the implanted correction lens is pressed against the natural lens, there will be no risk of adherence due to the small radius and since the curve is flawless, there will be no stress concentrations.

EXAMPLE 2

Figure 5:
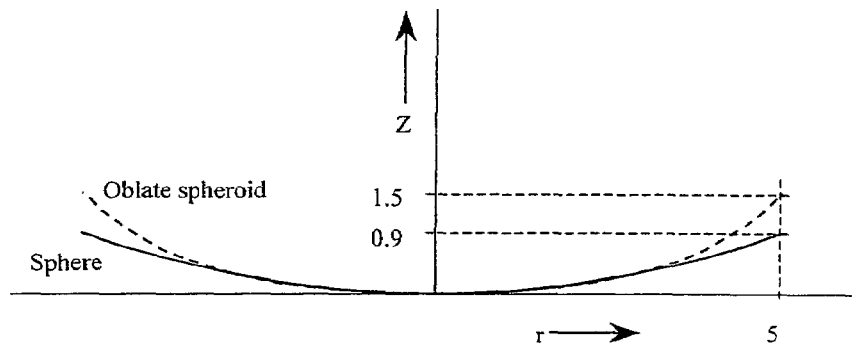
FIG. 5 shows the design of an oblate spheroid posterior surface.
Figure 6:
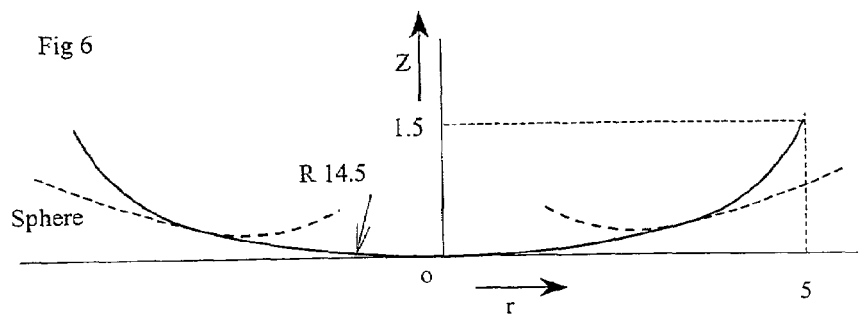
FIG. 6 shows a surface constructed by spheres.

A large radius of curvature of 14.5 mm is selected to avoid adherence with the central radius of the natural lens. A spherical posterior surface is drafted with 10 mm in diameter, a radius of curvature of 14.5 mm and a central vault of 0.9 mm. To obtain a central vault of 1.5 mm, the surface is constructed as an oblate spheroid following the formula:

$$z = cvr^2/(1+\sqrt{(1-cv^2(cc+1)r^2)})$$

with a conic constant $cc=7.2$. A rotation symmetric surface according to FIG. 5 is obtained with a 1.5 mm vault of the implant over a diameter of 10 mm. This surface will vault sufficiently over the natural lens and if the implanted lens will be pressed against the natural lens, there will be nor risk of adherence. Since the posterior surface will be flawless, the risk of stress concentration is eliminated. FIG. 6 shows an alternative design of a rotation symmetric posterior correction lens surface, according to which a curve is constructed in r-Z plane having a central circle segment with a radius of curvature of 14.5 mm is drafted. In the peripheries, circle segments with smaller radii of curvature are tangentially attached to the central segment to provide a flawless curve. A posterior surface having similar advantageous characteristics is thereby obtained.

EXAMPLE 3

Figure 7:
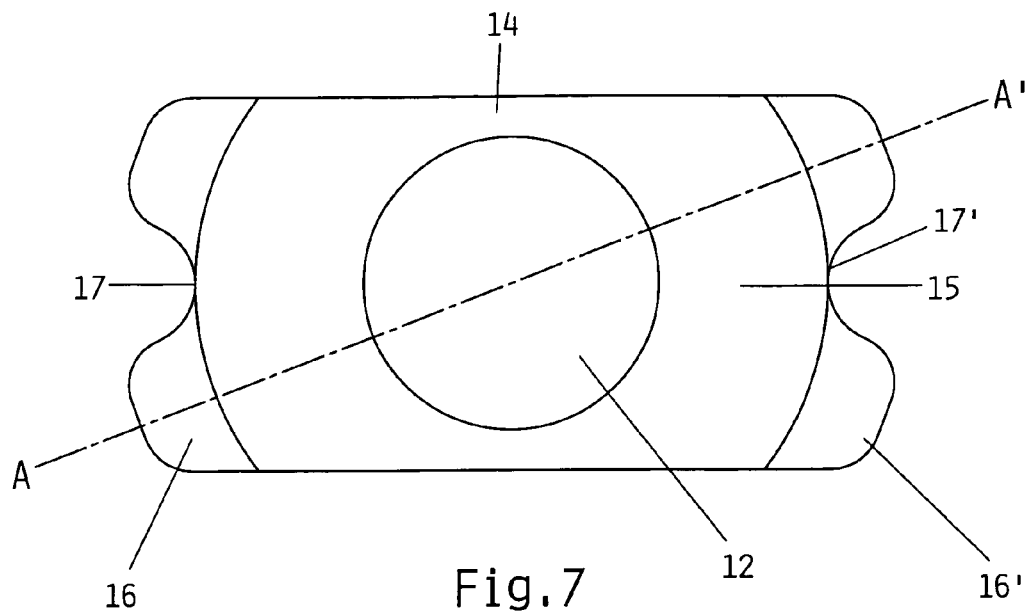
FIG. 7 shows a top view of an embodiment of the inventive corrective lenses

FIG. 7 shows a correction lens 10 lathe cut from a co-polymer of N-benzyl-N-methacrylamide with a refractive index of 1.49. The co-polymer is produced in accordance with U.S. Pat. No. 5,717,049. The lens has a maximum diameter of 12.5 mm and a central circular optical part 12 with a diameter of 6 mm and a support element 14. The support element consist of an inner part 15 surrounding the optical part and two peripheral parts 16 and 16' which after implantation will placed in the region of the ciliary sulcus of the eye and contribute to keep the lens in a central location. In this embodiment, the inner part has a diameter of 10 mm. The peripheral parts are each provided with a centrally located concave indentation 17, 17' that provide a free area for fluid circulation close to the ciliary sulcus.

Figure 1A:
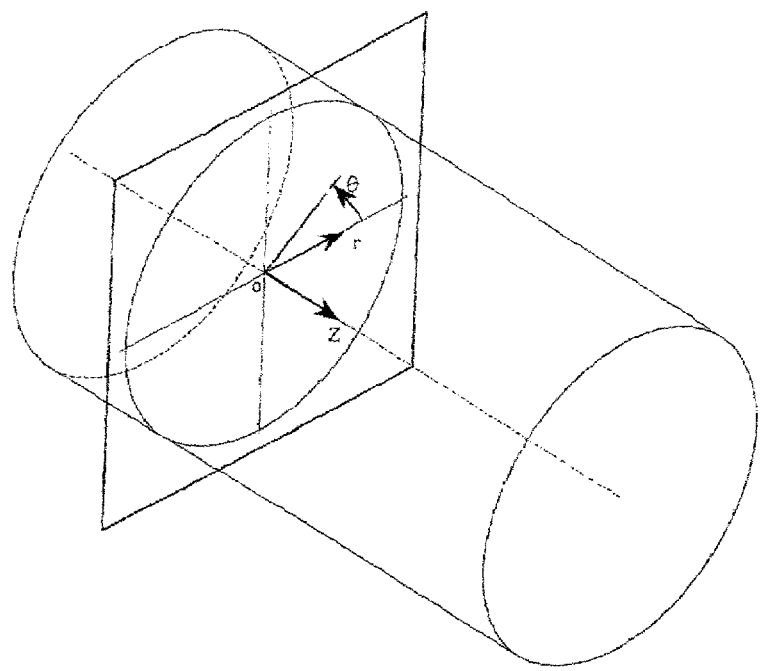
FIG. 1A shows a definition of the cylindrical coordinate system.
Figure 1B:
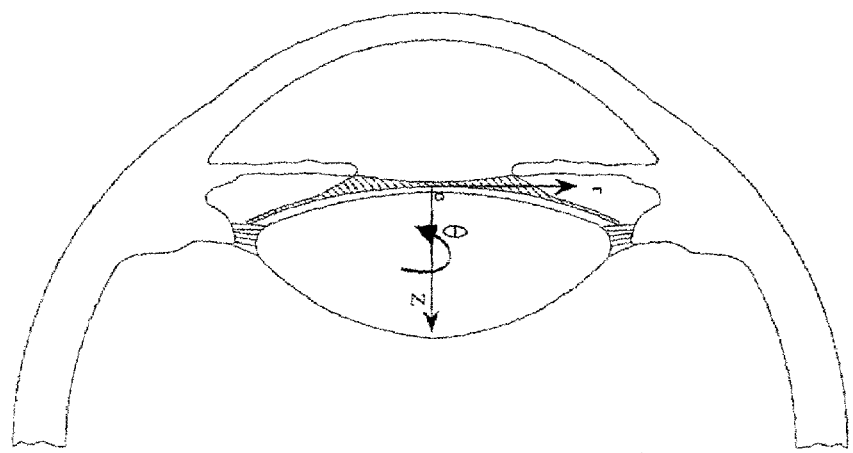
FIG. 1B shows the cylindrical coordinate system applied on a correction lens implanted in the eye.
Figure 2:
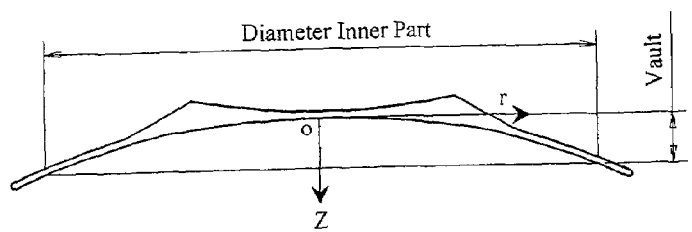
FIG. 2 shows a definition of the total lens vault.
Figure 8:
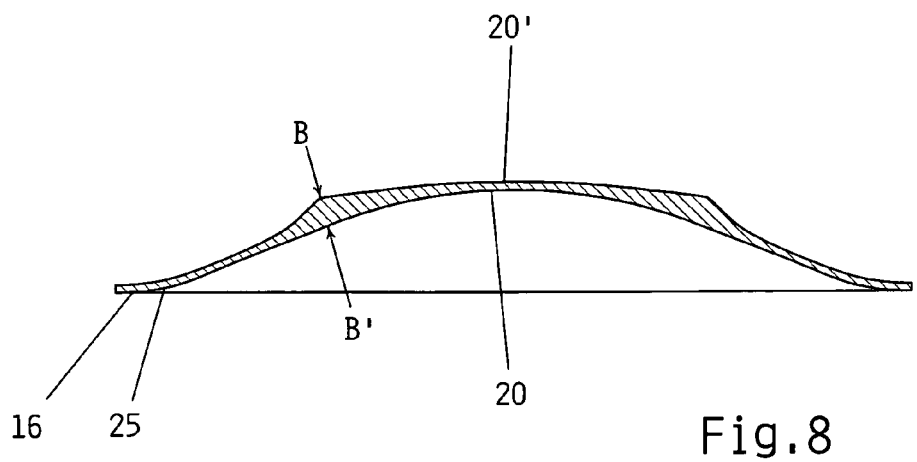
FIG. 8 shows a principal crossectional view along arrows A–A' in the embodiment of FIG. 1
Figure 9:
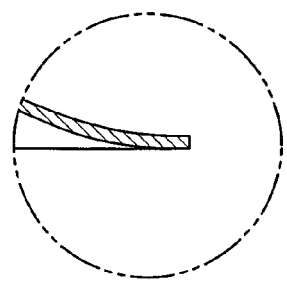
FIG. 9 is detailed crossectional view of the peripheral part of the support elements

FIG. 8 shows a crossectional plane containing the optical axis along arrows A–A' in FIG. 1. The intersection between this plane and the posterior surface of the lens represents a posterior curve that is arranged to be centrally flawless. As also demonstrated in FIG. 8, the optical part has a negative power of −12 diopters and an edge thickness shown long arrows B–B' of 0.45 mm. The maximum vault h of the lens is 1.7 mm. At a central position, in close proximity to the intersection with the optical axis 20–20', the radius of the posterior curve is 7 mm and thereby estimated to be substantially smaller than radius of the natural lens in its non-accommodated state. From the position close to optical axis, the posterior curve follows a parabolic curve having a curve formula $z = cvr^2/(1+\sqrt{(1-cv^2(cc+1)r^2)})$ with $cv=0.143$ mm$^{-1}$ and $cc=-3$. The posterior flawless curve extends over the peripheral part of the optical part and along the posterior side of the supporting element to a point 25, which is a point of inflection. From this point, at which the inner part of the support means changes to the peripheral parts, the posterior surface is bended outwards away from the zonulas attaching the natural lens. The posterior curve of the peripheral part 16 is converging towards a plane perpendicular to the optical axis. The peripheral part is shown in detail by FIG. 9.

The lens according to FIGS. 7 and 8, as described above, is designed to have reduced interference or disturbing contacts with the natural lens and may yet be designed with as large optical part as 6 mm and with a considerably low edge thickness. The posterior surface is free from areas or points that will create a local pressure on the natural lens when the correction lens moves in the posterior chamber during actions of self-centration when it touches the ciliary sulcus peripherally and the iris in an anterior direction. In addition, a parabolic posterior surface will enhance the centration of the lens due to its non-spherical design and its closer approximation of the natural lens when compared to an ellipsoid posterior surface. During accommodation, the shape of a young crystalline lens will change from a substantially spherical shape to a parabolic shape. At the same time, displaced aqueous fluid between the correction lens and the natural lens will exert a pressure both radial and axial pressure on the correction lens. The resulting force at a certain location of the correction lens will depend on the proximity to the natural lens. A close distance between the lenses will generate large forces on the correction lens and in this manner centering forces will be exerted on the correction lens during accommodation. For elder patients, who have lost their capability of accommodation, Thus, a lens with parabolic posterior surface, with a central radius larger than the central radius of the natural lens, can easily be centrated, as opposed to lenses with spherical or ellipsoid posterior surfaces.

The invention claimed is:

1. A method of selecting a suitable implantable correction lens for implantation in the posterior chamber of an eye between the iris and the intact natural lens, the correction lens comprising a centrally located optical part capable of providing an optical correction and a peripherally located supporting element capable of maintaining said optical part in said central location, wherein said optical part and said support element together have a concave posterior surface which is part of a non-spherical surface that is rotation symmetric around the optical axis of said optical part, wherein the intersection between said non-spherical surface and any plane containing the optical axis represents a flawless curve free from discontinuities and points of inflection, the method comprising the steps of:
  (i) determining the power of optical correction;
  (ii) estimating the anterior radius of the natural lens in its non-accommodated state;
  (iii) selecting a posterior central radius of the correction lens different from that of the natural lens in its non-accommodated state;
  (iv) determining the total lens vault based on the data arriving from steps (ii) and (iii); and
  (v) selecting a flawless curve free from points of inflection representing the interaction of the posterior surface and a plane containing the optical axis so as to provide an aspheric posterior lens surface.

2. A method according to claim 1 comprising the step of measuring the anterior chamber depth and considering this value together with the data arriving from steps (ii) and (iii) in the determination of the total lens vault.

3. A method according to claim 1, wherein the anterior chamber depth is measured in both accommodated and non-accommodated states of the eye.

4. A method according to claim 1 further comprising the steps of estimating the length of ciliary sulcus and determining the maximum lens diameter.

5. A method according to claim 1, comprising the estimation of the anterior radius of the natural lens in its accommodated state and from this value in combination with the data arriving from steps (ii) and (iii) determining a maximum lens vault having a sufficient safety margin for avoiding contacts between the natural lens and the posterior surface of the correction lens.

6. A method of obtaining a suitable intraocular correction lens implantation for an eye, comprising the steps of:
  (i) determining the power of optical correction;
  (ii) estimating the anterior radius of the natural lens in its non-accommodated state;
  (iii) selecting a posterior central radius of the correction lens different from that of the natural lens in its non-accommodated state;
  (iv) determining the total lens height from the data arriving from steps (ii) and (iii); and
  (v) selecting a lens from a kit of correction lenses, wherein each lens is adapted for implantation in the posterior chamber of an eye between the iris and the intact natural lens and comprises a centrally located optical part capable of providing an optical correction and a peripherally located supporting element capable of maintaining said optical part in said central location, wherein said optical part and said support element together have a concave posterior surface which is part of a non-spherical surface that is rotation symmetric around the optical axis of said optical part, wherein the intersection between said non-spherical surface and any plane containing the optical axis represents a flawless curve free from discontinuities and points of inflection, said kit containing lenses with a range of different optical powers with dimensional features resulting from the estimation of a suitable average population.

7. A method according to claim 6, wherein said selection is based on employing an algorithm capable of transferring the physiological data to a suggested lens and from this result select the most appropriate lens present in the kit.

8. A method according to claim 6 comprising the step of measuring the anterior chamber depth and considering this value together with the data arriving from steps (ii) and (iii) in the determination of the total lens vault.

9. A method according to claim 8, wherein the anterior chamber depth is measured in both accommodated and non-accommodated states of the eye.

10. A method according to claim 6, comprising the estimation of the anterior radius of the natural lens in its accommodated state and from this value in combination with the data arriving from steps (ii) and (iii) determining a maximum lens vault having a sufficient safety margin for avoiding contacts between the natural lens and the posterior surface of the correction lens.

11. A method according to claim 6 further comprising the steps of estimating the length of ciliary sulcus and determining the maximum lens diameter.

12. A method according to claim 11, comprising the step of cutting the lens into a determined maximum diameter before implantation by means of mechanical tools.

13. A method according to claim 11, comprising the step of cutting the lens into a determined maximum diameter by means of an ophthalmic excimer laser.

14. An intraocular correction lens adapted for implantation in the posterior chamber of an eye between the iris and the intact natural lens, comprising a centrally located optical part capable of providing an optical correction and a peripherally located supporting element capable of maintaining said optical part in said central location, wherein said optical part and said support element together have a concave posterior surface which is part of a non-spherical surface that is rotation symmetric around the optical axis of said optical part, wherein the intersection between said non-spherical surface and any plane containing the optical axis represents a flawless curve free from discontinuities and points of inflection.

15. A correction lens according to claim 14, wherein the flawless curve is at least extended in a direction towards the lens periphery within an area defined by the projection of a natural lens in an eye in which the lens is adapted for implantation, on the posterior surface of said correction lens in a direction parallel to the optical axis.

16. A correction lens according to claim 15, wherein the flawless curve is at least extended in a direction towards the lens periphery within an area defined by the projection of the zonula-free natural lens on the posterior surface of said correction lens in a direction parallel to the optical axis.

17. A correction lens according to claim 15, wherein the flawless curve has substantially the same extension as the width of the lens.

18. A correction lens according to claim 15, wherein the supporting element comprises an inner part and a peripheral part designed so as to be at least partially in contact with a ciliary sulcus and zonulas in an eye in which the correction lens is adapted for implantation.

19. A correction lens according to claim 18, wherein the peripheral part is flawlessly connected to the inner part.

20. A correction lens according to claim 19, wherein the peripheral part follows a curve diverging towards a plane perpendicular to the optical axis.

21. A correction lens according to claim 18, wherein the peripheral part is connected to the inner part at a point of inflection.

22. A correction lens according to claim 21, wherein the peripheral part follows a curve diverging towards a plane perpendicular to the optical axis.

23. A correction lens according to any of claims 18 to 21, wherein the peripheral part follows a curve diverging towards a plane perpendicular to the optical axis.

24. A correction lens according to claim 18, wherein the peripheral part of the support means consists of two separate diametrically opposite, symmetrical parts, each provided with at least one peripherally located indentation of a generally concave shape extending inwards towards the inner part of the support means and the optical axis.

25. A correction lens according to claim 24, wherein the indentation extends to the inner part of the support means.

26. A correction lens according to claim 24, wherein the indentation has a depth of about 0.5 to 1.25 mm.

27. A correction lens according to claim 18, wherein the flawless curve extends along the inner part of the supporting element.

28. A correction element according to claim 18, wherein the peripheral part of support element is provided with a higher flexibility than the inner part.

29. A correction lens according to claim 14, wherein the central radius of the posterior surface of the optical part is adapted to be different from the central radius of a natural lens in an eye in which the correction lens is adapted for implantation, in a non-accommodated state.

30. A correction lens according to claim 29, wherein the central radius of the posterior surface is substantially smaller than the central radius of the natural lens.

31. A correction lens according to claim 30, wherein the central radius of the posterior surface is less than about 7 mm.

32. A correction lens according to claim 29, wherein the central radius of the posterior surface is substantially larger than the central radius of the natural lens.

33. A correction lens according to claim 32, wherein the central radius of the posterior surface is larger than about 14 mm.

34. A correction lens according to claim 29, wherein the radius of the posterior surface increases from the central part towards the lens periphery.

35. A correction lens according to claim 29, wherein the maximum lens vault is sufficiently large so as to avoid contacts between the posterior surface and the natural lens in its accommodated state.

36. A correction lens according to claim 14, wherein the flawless curve comprises two or more tangentially attached circle segments.

37. A correction lens according to claim 36, wherein the flawless curve comprises three tangentially attached circle segments.

38. A correction lens according to claim 37, wherein the three tangentially attached circle segments consist of a centrally located segment having a radius different from that of a natural lens in an eye in which the correction lens is adapted for implantation in its non-accommodated state and two peripheral segments.

39. A correction lens according to claim 38, wherein the centrally located segment corresponds to the optical part and the peripheral segments correspond to the inner part of the support element.

40. A correction lens according to claim 39, wherein the three tangentially attached circle segments together approximate an ellipsoidal curve.

41. A correction lens according to claim 14, wherein the flawless curve substantially follows the curve formula $z=cvr^2/(1+\sqrt{(1-cv^2(cc+1)r^2)})$, where z is the axial coordinate of the curve, r is the radial coordinate of the curve, cv is the reciprocal central radius of the optical part and cc is the conic constant to shape the curve which not is equal to zero.

42. A correction lens according to claim 14, wherein, the flawless curve representing the posterior is a spline polynome constructed from non-uniform rational B-splines (NURBS).

43. A correction lens according to claim 14, having a total diameter less than the average diameter of the ciliary sulcus.

44. A correction lens according to claim 14, wherein the optical part has a diameter of a size sufficient to avoid edge glare.

45. A correction lens according to claim 44, wherein the optical part has a diameter of at least 5.5 mm.

46. A correction lens according to claim 44 having an optical power larger than ±15 diopters.

47. A kit of intraocular lenses with a suitable variety of optical powers, wherein each individual lens is provided with the features according to any of claims 14 to 35.

48. An intraocular correction lens adapted for implantation in the posterior chamber of an eye between the iris and the intact natural lens, comprising a centrally located optical part capable of providing an optical correction and a peripherally located supporting element capable of maintaining said optical part in said central location, wherein said optical part and said support element together have a concave posterior surface which is part of a non-spherical surface that is rotation symmetric around the optical axis of said optical part, wherein the intersection between said non-spherical surface and any plane containing the optical axis represents a flawless curve free from discontinuities and points of inflection, wherein the flawless curve substantially follows the curve formula $z=cvr^2/(1+\sqrt{(1-cv^2(cc+1)r^2)})$, where z is the axial coordinate of the curve, r is the radial coordinate of the curve, cv is the reciprocal central radius of the optical part and cc is the conic constant to shape the curve which is not equal to zero.

49. A correction lens according to claim 48, wherein the curve formula is adjusted with one or several additional polynomal factors $a_1r^4+a_2r^6+a_3r^8+a_4r^{10}+ \ldots +a_nr^{2(n-1)}$, wherein $a_1, a_2, a_3, a_4, \ldots a_n$ are aspheric constants, thereby generating the curve formula $z=cvr^2/(1+\sqrt{(1-cv^2(cc+1)r^2)})+a_1r^4+a_2r^6+a_3r^8+a_4r^{10}+ \ldots +a_nr^{2(n-1)}$.

50. A correction lens according to claim 49, wherein the flawless curve has a central radius proximal to the optical axis less than the radius of a natural lens in the eye of an individual in which the correction lens is adapted for implantation, in its non-accommodated state, said curve substantially following a parabolic or hyperbolic curve formula.

51. A correction lens according to claim 49, wherein the flawless curve has a central radius proximal to the optical axis larger than the radius of a natural lens in the eye of an individual in which the correction lens is adapted for implantation in its non-accommodated state, said curve substantially following an ellipsoidal curve formula.

52. A correction lens according to claim 48, wherein the flawless curve has a central radius proximal to the optical axis less than the radius of a natural lens in an eye in which the correction lens is adapted for implantation, in its non-accommodated state, said curve substantially following a parabolic or hyperbolic curve formula.

53. A correction lens according to claim 48, wherein the flawless curve has a central radius proximal to the optical axis larger than the radius of a natural lens in an eye in which the correction lens is adapted for implantation in its non-accommodated state, said curve substantially following an ellipsoidal curve formula.

54. An intraocular correction lens adapted for implantation in the posterior chamber of an eye between the iris and the intact natural lens, comprising a centrally located optical part capable of providing an optical correction and a peripherally located supporting element capable of maintaining said optical part in said central location, wherein said optical part and said support element together have a concave posterior surface which is part of a non-spherical surface that is rotation symmetric around the optical axis of said optical part, wherein the intersection between said non-spherical surface and any plane containing the optical axis represents a flawless curve free from discontinuities and points of inflection, wherein the flawless curve representing the posterior is a spline polynome constructed from non-uniform rational B-splines (NURBS).

* * * * *

UNITED STATES PATENT AND TRADEMARK OFFICE
CERTIFICATE OF CORRECTION

| | | |
|---|---|---|
| PATENT NO. | : 7,048,759 B2 | Page 1 of 1 |
| APPLICATION NO. | : 09/777510 | |
| DATED | : May 23, 2006 | |
| INVENTOR(S) | : Theo T.M. Bogaert et al. | |

It is certified that error appears in the above-identified patent and that said Letters Patent is hereby corrected as shown below:

Claim 23, column 15, line 14, change "any one of claims 18 and 21," to --claim 18,--.

Claim 41, column 16, lines 11-16, delete in its entirety.

Claim 42, column 16, lines 17-20, delete in its entirety.

Claim 47, column 16, lines 31-32, change "provided with the features according to any of claims 14 to 35." to --according to claim 14.--.

Signed and Sealed this

Nineteenth Day of December, 2006

JON W. DUDAS
*Director of the United States Patent and Trademark Office*